United States Patent [19]

Miller

[11] Patent Number: 4,490,352

[45] Date of Patent: * Dec. 25, 1984

[54] ENCAPSULATED EFFICACIOUS ZINC PHOSPHIDE RODENTICIDE

[75] Inventor: George T. Miller, Lewiston, N.Y.

[73] Assignee: Occidental Chemical Corporation, Niagara Falls, N.Y.

[*] Notice: The portion of the term of this patent subsequent to Mar. 8, 2000 has been disclaimed.

[21] Appl. No.: 434,805

[22] Filed: Oct. 18, 1982

Related U.S. Application Data

[63] Continuation-in-part of Ser. No. 256,742, Apr. 23, 1981, Pat. No. 4,376,112.

[51] Int. Cl.³ .............................................. A01N 59/26
[52] U.S. Cl. ........................................ 424/17; 424/32; 424/78; 424/128
[58] Field of Search ...................... 424/17, 78, 32, 128

[56] References Cited

U.S. PATENT DOCUMENTS 4,376,112  3/1983  Miller .................................... 424/17

Primary Examiner—Delbert R. Phillips
Assistant Examiner—F. Moezie
Attorney, Agent, or Firm—James F. Tao; William G. Gosz

[57] ABSTRACT

A rodenticide is disclosed comprising an encapsulated zinc phosphide toxicant, a bait, and a binder for adhering the encapsulated zinc phosphide to the bait, said binder comprising a polyol or a sugar-containing fluid. The encapsulant is a thermoplastic polyamide, preferably nylon, present in an amount of from about 2% to about 10% by weight of zinc phosphide. When the bait is a grain or a processed grain, a zinc salt is preferably added to the rodenticide to inhibit the generation of phosphine. Histamine, a histamine salt or a histamine-producing substance, such as red pepper, can also be added to the rodenticide to stimulate acid secretion in the stomach of the rodent.

A particulate encapsulated product is also disclosed comprising a core of zinc phosphide having a coating of a thermoplastic polyamide present in the range of from about 2% to about 10% by weight. The encapsualted product is a small particle capable of passing through a 40 mesh size screen.

21 Claims, No Drawings

ENCAPSULATED EFFICACIOUS ZINC PHOSPHIDE RODENTICIDE

CROSS-REFERENCE TO RELATED APPLICATION

This application is a continuation-in-par of U.S. application Serial No. 256,742, filed Apr 23, 1981, now U.S. Pat. No. 4,376,112.

BACKGROUND OF THE INVENTION

This invention relates to an efficacious and safe method of controlling rodent population. Rodents, especially Norway rats common to the United States, roof rats, black rats, ground squirrels, prairie dogs, mountain beaver, etc., feed on a wide variety of foods. Rats, in particular, do a tremendous amount of damage by their eating habits, destroying agricultural crops, stored grain and stored produce, as well as contributing to the spread of disease through their infestation of urban areas. Attempts to control or eliminate rodents have been made for many years. Because the rodents quickly learn to avoid the poisons and poison impregnated foods, the use of poisoned food or baits as practiced to date does not provide a long term solution to the rodent problem.

The need for economical rodent control methods for agricultural, commensal and industrial uses, necessitates a material that can be easily dispersed in the fields or in buildings and provide an efficacious long term method of rodent control. Many of the baits depend upon the impregnation of seeds, fruits, peanut butter, etc. with a poison. The rodents quickly learn to avoid such poison bait by the odor or taste, particularly when the discomfort of the ingestion of a sub-lethal quantity is associated with the bait. Therefore, it is advantageous to prepare a poison that has its odor and taste effectively masked and the onset of the reaction to the poison is delayed until a lethal amount is consumed and the rodent has left the bait area.

Attempts to encapsulate rodenticides have been made but generally enough rodenticide is entrapped in the encapsulating material or will permeate through it to allow the rodent to identify the fact that a poison is present. Also, methods have been developed to prepare enteric coated rodenticides. See, for example, Shuyler U.S. Pat. No. 2,957,804 wherein a rodenticide, such as zinc phosphide, is surrounded by a resin material that will dissolve in the alkaline condition of the rodent's intestines rather than the acidic conditions of the rodent's stomach. The theory is that the rodent that has eaten the poison would not realize that it was deadly since there would be considerable time delay from the ingestation to death, and thus would not avoid the enteric coated material. In order to accomplish this result, Shuyler utilizes a relatively thick coating wherein the coating is essentially present in an amount of at least about 50% of the weight of the rodenticide. The efficacy of such encapsulated material has been shown to be no more than unencapsulated material because the amount of encapsulant needed to mask the material also decreases its availability as a poison. More importantly, the zinc phosphide does not react substantially in alkaline environments to produce phosphine.

Zinc phosphide is well known as a rodenticide and is especially effective when used against rats and field mice. Zinc phosphide is a dark grey crystalline material with a faint garlic-like odor and is a very stable compound when stored in a dry state. It is substantially insoluble in water, but reacts with acid to produce phosphine, a deadly poison. It is effective against many species of rodents. However, it suffers from the disadvantage that rodents easily identify it in a bait and avoid it. Zinc phosphide is considered one of the safest rodenticides to control rats and mice because of its emetic properties and the fairly rapid dissipation of the poison in the rodent's body. Thus, children, domestic animals, etc. will regurgitate the poison before it is lethal, whereas rodents cannot regurgitate. Zinc phosphide in the body of a dead rodent reacts with the fluids in the rodent's body and is consumed in a way which eliminates the hazard of secondary poisoning of other animals who may eat the dead rodent. For this reason zinc phosphide has been widely used for controlling rodents in agriculture so as to protect rice, sugarcane and other growing plants against attack. In the western United States, for example, zinc phosphide has had widespread use to control ground squirrels, and the like.

In co-pending U.S. application Ser. No. 256,742, it was discovered that when particles of zinc phosphide are coated with from about 2% to about 10% by weight of a thermoplastic polyamide, such encapsulation masks the odor and taste of the toxicant so as to avoid detection by the rodent, while at the same time increasing its efficacy as a rodenticide by allowing the phosphide to be released in the stomach of the rodent to generate a lethal dose of phosphine.

Although it has been demonstrated that encapsulated zinc phosphide can provide an effective rodenticide, further investigation and experimentation has suggested additional improvements to increase the efficacy of the rodenticide, primarily as a result of improvements to the binder and bait comprising the rodenticide, as well as by including additives in the formulation.

For instance, in formulating rodenticidal compositions, it is commonplace to use oils, such as corn oil, as a binder for adherence of the toxicant to the bait or food. Without a binder, the zinc phosphide would tend to sink to the bottom of the bait and not be eaten by the rodent. The use of corn oil as a binder is required in EPA formulations. However, it has been observed that corn oil actually decreases the efficacy of the toxicant by forming an additional coating on the encapsulated zinc phosphide preventing release of the zinc phosphide in the rodent's stomach.

Another problem has been encountered when zinc phosphide is added to certain bait compositions which contain grains or processed grains. It has been found that when the zinc phosphide is added to these bait compositions, phosphine is generated resulting in rejection of the bait by the rodent.

It is thus a primary object of the present invention to provide an improved rodenticide which substantially overcomes the problems heretofore associated with the use of zinc phosphide as a toxicant in formulated bait compositions.

SUMMARY OF THE INVENTION

The present invention is directed to an improved rodenticide based on the use of encapsulated zinc phosphide ($Zn_3P_2$) as a toxicant. The zinc phosphide, which has been coated with from about 2% to about 10% by weight of a thermoplastic polyamide, is added to a bait composition and mixed with a binder. The binders used in the present invention are those which are dissolvable in the rodent's stomach to allow release of the toxicant and include polyols and sugar-containing fluids. Zinc salts, such as zinc oxide (ZnO), are added to baits containing grains or processed grains to prevent liberation of phosphine and rejection by the rodent. Histamine, a histamine salt or a histamine-producing substance, can also be added to the rodenticide to stimulate the production of gastric juice by the rodent further increasing the efficacy of the rodenticide.

In another aspect, this invention is also directed to a particulate encapsulated product comprising zinc phosphide coated with from about 2% to about 10% by weight of a thermoplastic polyamide, the product being capable of passing through a 40 mesh size screen, preferably a 100 mesh size screen.

DETAILED DESCRIPTION OF THE INVENTION

The improved rodenticide of this invention comprises a toxicant, a bait, and a binder for adhering the toxicant to the bait. phosphide ($Zn_3P_2$) in particulate form The toxicant is zinc which is encapsulated or coated with from about 2% to about 10% by weight of zinc phosphide of a thermoplastic polyamide. The thermoplastic polyamide must be capable of being removed, i.e. dissolvable, in the acidic environment of the rodent's stomach at least to the extent of exposing a lethal dose of the zinc phosphide. The lethal dose of this invention for Norway rats is approximately 30 mg. zinc phosphide per Kilogram of body weight of rodent. The thermoplastic polyamides which are preferred for use in accordance with this invention are the nylons, especially nylon 6, nylon 66, nylon 6-10 and nylon 6-12. However, others including nylons 1, 2, 3, 4, 5, 7, 8, 9, 10, 77 and substituted polyamides which have solubility characteristics rendering them suitable, depending upon the thickness of the coating applied, may be used.

The encapsulated zinc phosphide particles which are useful in this invention are preferably 40 mesh size, i.e. they are capable of passing through a 40 mesh screen, and most preferably 100 mesh size.

There are many techniques that may be used for coating the thermoplastic polyamide polymer onto the rodenticide, such as pan coating, spraying onto moving particles, spray drying, solvent evaporation, belt coating and others. The selection of the coating technique will be dependent upon the variables associated with the polymer, e.g. economics, quality, equipment availability, etc. A preferred method is to dissolve the polymer in a suitable solvent, which solvent will not dissolve or react with the zinc phosphide. The solvent is removed from the slurry of zinc phosphide in the solution by evaporation.

The bait which can be used in practicing this invention comprises a variety of foods or attractants and taste enhancers, such as sugar. Various grains, such as oats, corn, barley and rice, diced vegetables or fruit, processed grains such as bread, crackers and cereals, and grasses such as hay.

In the case of grains and processed grains, it has been found that when the coated zinc phosphide toxicant is mixed with the bait, phosphine is generated causing rejection of the bait (bait shyness) by the rodent. One possible explanation of this phenomenon would be that the phosphine is produced by the reaction of phytic acid and/or phospholipids contained in the grain. In any event, it has now been discovered that the liberation of phosphine resulting from mixing the toxicant with such baits can be substantially prevented by adding a zinc salt to the bait prior to or during admixture of the bait and toxicant. Operable zinc salts include, but are not limited to, zinc oxide (ZnO), zinc chloride, zinc sulfate, zinc carbonate, basic zinc carbonate, zinc hydroxide, zinc resinate, zinc gluconate, or the like, and mixtures thereof. Presumably, the zinc salt reacts preferentially with the phytic acid or phospholipid to prevent reaction with the zinc phosphide, although applicant does not wish to be bound by any particular theory of operability. Effective amounts of zinc oxide are from about 0.001% to about 1.0%, preferably from about 0.1% to about 0.2%, by weight of bait.

The binder of this invention is a substance which will physically bind or adhere the toxicant to the bait. In addition, for purposes of this invention, the binder must be soluble in the acidic environment of the rodent's stomach. For example, although corn oil is an effective adhesive, and is, in fact, recommended as a binder by the EPA, it is essentially insoluble under such acidic conditions, and thus inhibits release of the zinc phosphide in the rodent's stomach. Thus, the use of binders such as corn oil would obviously defeat the very objective of this invention, namely release of the toxicant in the rodent's stomach.

Those binders which have been found particularly effective in the practice of this invention include polyols, and particularly glycols such as ethylene glycol, propylene glycol, polyethylene glycol and polypropylene glycol, as well as various sugar-containing fluids, such as caramel, molasses, and the like. The amount of binder required is not critical and will usually be in the range of from about 5% to about 10% by weight of bait.

It has been found that the effectiveness of the rodenticide can be significantly enhanced by incorporating into the rodenticide a gastric juice stimulant. The purpose of such stimulant is to increase the acid concentration in the rodent's stomach and thereby promote the release of the toxicant. Stimulants which serve this purpose include histamine, histamine salts such as histamine hydrochloride, or histamine-producing substances such as beef bouillion and red pepper which are preferably present in the range of from about 0.005% to about 0.1% by weight of bait. When such a stimulant is used in combination with a zinc salt, it has been found that up to 2% by weight of the zinc salt can be effectively utilized.

The rodenticide preferably contains from about 0.2% to about 5% encapsulated zinc phosphide by weight of bait, and most preferably from about 1% to about 2%, although greater or lesser amounts can also be used.

The following examples are given to further illustrate the invention. However, they are not intended to limit the scope thereof except as defined by the appended claims.

EXAMPLE 1

In a 2-liter resin flask reactor, equipped with stirrer, is placed 1800 ml dimethylformamide, 500 grams zinc phosphide and 25 grams nylon 6-12. The mixture is stirred and heated to reflux (150° C.) to dissolve the nylon. The excess dimethylformamide is then distilled off under vacuum at approximately 60° C. After most of the dimethylformamide is distilled off, the temperature is increased to 175° C. with continued agitation. The solids go through a pasty consistency and then become a flowing powder, as the last of the solvent is evaporated. The vapor space was purged with nitrogen to remove the last traces of solvent. A yield of 514 grams of free-flowing 5% by weight nylon coated zinc phosphide powder was obtained.

EXAMPLE 2

A rodenticide was formulated by mixing 1% by weight of unencapsulated zinc phosphide with EPA bait. The EPA bait contained 65% by weight of ground corn, 25% by weight of rolled oats, 5% by weight of powdered sugar and 5% by weight of corn oil. The rodenticide was fed to Norway rats under choice test conditions in which a bowl of unpoisoned placebo and a bowl of placebo treated with the rodenticide of this invention were placed in the cage with the rat under test. A total of 30 rats were evaluated under these choice test conditions in groups of five rats per test. 16 of the 30 rats tested, or approximately 53%, were killed.

EXAMPLE 3

Following the procedures of Examples 1 and 2, a rodenticide was formulated by mixing 1% by weight of powdered zinc phosphide coated with 5% by weight of nylon 6–12 with EPA bait. The rodenticide was again fed to a total of 55 Norway rats under choice test conditions. Thirty-six (36) of the 55 rats tested, or approximately 65%, were killed.

EXAMPLE 4

A rodenticide was prepared following the procedure of Example 3 except that the zinc phosphide was coated with 50% by weight of nylon 6–12. The rodenticide was fed to 5 rats under choice test conditions. None of the rats were killed.

A comparison of the results of Examples 2 and 3 shows that only 53% of the rodents were killed when tested using a rodenticide having an unencapsulated zinc phosphide toxicant, while 65% of the rodents were killed when tested using a rodenticide having a zinc phosphide toxicant coated with 5% nylon 6–12.

A comparison of the results of Examples 3 and 4 shows that while 65% of the rodents were killed when tested using a rodenticide having a zinc phosphide toxicant coated with 5% nylon 6–12, none of the rodents were killed when tested using a rodenticide having a zinc phosphide toxicant coated with 50% nylon 6–12.

EXAMPLE 5

A rodenticide was prepared following the procedure of Example 3 except that propylene glycol was substituted for corn oil in the EPA bait in the same weight proportion. The rodenticide was fed to a total of 45 Norway rats under choice test conditions. Thirty-nine (39) of the 45 rats tested, or approximately 87%, were killed.

EXAMPLE 6

A rodenticide was prepared following the procedure of Example 5 except that 0.01% histamine hydrochloride by weight of bait was added. The rodenticide was fed to a total of 10 rats under choice test conditions. Nine (9) of the 10 rats, or 90%, were killed.

EXAMPLE 7

Example 6 was repeated except that 0.03% histamine hydrochloride was used. The rodenticide was fed to 5 rats under choice test conditions. All of the rats (100%) were killed.

EXAMPLE 8

Example 6 was repeated except that 0.05% histamine hydrochloride was used. The rodenticide was fed to 10 rats under choice test conditions. Nine (9) of the 10 rats (90%) were killed.

EXAMPLE 9

A rodenticide was prepared following the procedure of Example 5 except that 0.2% ZnO by weight of bait was added. The rodenticide was fed to 5 rats under choice test conditions. All of the rats (100%) were killed.

EXAMPLE 10

A rodenticide was prepared following the procedure of Example 5 except that 0.01% histamine hydrochloride and 0.2% ZnO both by weight of bait were added. The rodenticide was fed to 5 rats under choice test conditions. All of the rats (100%) were killed.

EXAMPLE 11

Example 10 was repeated except that 0.02% histamine hydrochloride and 0.2% ZnO were used. The rodenticide was fed to 10 rats under choice test conditions. All of the rats (100%) were killed.

EXAMPLE 12

Example 10 was repeated except that 0.01% histamine hydrochloride and 2.0% ZnO were used. The rodenticide was fed to 5 rats under choice test conditions. Four (4) of the 5 rats, or 80%, were killed.

A comparison of the results of Example 3 and Example 5–14, which illustrate rodenticides prepared according to the present invention, shows that significant improvements in rodent mortality are achieved using the various improvements and modifications of the present invention.

While particular embodiments of the invention have been shown and described herein, modifications and variations thereof will occur to those skilled in the art. It is to be understood, therefore, that the appended claims are intended to cover such modifications and variations which are within the true scope and spirit of this invention.

What is claimed is:

1. A particulate encapsulated product comprising a core of zinc phosphide and a coating of a thermoplastic polyamide, said polyamide being present in the range of from about 2% to about 10% by weight of zinc phosphide, said encapsulated product being capable of passing through a 40 mesh screen.

2. The encapsulated product of claim 1 which is capable of passing through a 100 mesh screen.

3. A rodenticide comprising an effective amount of zinc phosphide coated with from about 2% to about 10% by weight of a thermoplastic polyamide, a bait, and a binder for adhering the coated zinc phosphide to the bait, said binder comprising a polyol or a sugar-containing fluid present in an amount of from about 5% to about 10% by weight of bait, the coated zinc phosphide being present in an amount of from about 0.2% to about 5% by weight of bait.

4. The rodenticide of claim 3 wherein the coated zinc phosphide is present in an amount of from about 1% to about 2% by weight of bait.

5. The rodenticide of claim 3 wherein the polyamide is nylon.

6. The rodenticide of claim 5 wherein the nylon is nylon 6–12.

7. The rodenticide of claim 5 wherein the nylon is nylon 66.

8. The rodenticide of claim 5 wherein the nylon is nylon 6–10.

9. The rodenticide of claim 5 wherein the nylon is nylon 6.

10. The rodenticide of claim 3 wherein the zinc phosphide is coated with about 5% by weight of polyamide.

11. The rodenticide of claim 3 wherein the binder comprises a glycol.

12. The rodenticide of claim 11 wherein the binder comprises propylene glycol or ethylene glycol.

13. The rodenticide of claim 11 wherein the binder comprises polyethylene glycol or polypropylene glycol.

14. The rodenticide of claim 11 wherein the binder comprises molasses.

15. The rodenticide of claim 11 wherein the binder comprises caramel.

16. The rodenticide of claim 3 wherein the bait comprises a grain or a processed grain.

17. The rodenticide of claim 16 wherein the bait further comprises a zinc salt or zinc oxide present in an amount of from about 0.001% to about 1% by weight of bait.

18. The rodenticide of claim 17 wherein the zinc salt is zinc oxide.

19. The rodenticide of claim 18 wherein the zinc oxide is present in an amount of from about 0.1% to about 0.2% by weight of bait.

20. The rodenticide of claim 3 which further comprises a stimulant selected from the group consisting of histamine, a histamine salt, beef bouillon and red pepper, said stimulant being present in an amount of from about 0.005% to about 0.1% by weight of bait.

21. A rodenticide comprising an effective amount of zinc phosphide coated with from about 2% to about 10% by weight of a thermoplastic polyamide, a bait comprising a grain or a processed grain, from about 5% to about 10% by weight of a binder comprising a polyol or a sugar-containing fluid, from about 0.001% to about 1% by weight of zinc oxide, and from about 0.005% to about 0.1% of histamine or a histamine salt, the coated zinc phosphide being present in an amount of from about 0.2% to about 5% by weight of bait.

* * * * *